United States Patent [19]

Kanehira et al.

[11] Patent Number: 4,872,458
[45] Date of Patent: Oct. 10, 1989

[54] THERMOTHERAPY APPARATUS

[75] Inventors: Katsuyuki Kanehira; Syuichi Takayama; Atsushi Amano; Hiroki Hibino; Naoki Uchiyama; Akio Nakada, all of Tokyo, Japan

[73] Assignee: Olympus Optical Co., Ltd., Tokyo, Japan

[21] Appl. No.: 94,377

[22] Filed: Sep. 8, 1987

[30] Foreign Application Priority Data

Sep. 16, 1986 [JP] Japan .................. 61-217517
Sep. 16, 1986 [JP] Japan .................. 61-217518

[51] Int. Cl.$^4$ ............................................. A61F 7/12
[52] U.S. Cl. ............................... 128/401; 128/303.1; 128/6; 128/344
[58] Field of Search .............. 128/401, 402, 403, 399, 128/343, 344, 303.12, 4, 6, 395, 396, 397, 303.1; 219/354, 553; 126/204

[56] References Cited

U.S. PATENT DOCUMENTS

| 2,303,873 | 12/1942 | Anderson | 219/354 |
| 2,387,258 | 10/1945 | Hague | 128/403 |
| 4,277,535 | 10/1980 | Connor | 128/401 |
| 4,402,311 | 9/1983 | Hattori | 128/4 |
| 4,409,993 | 10/1983 | Furihata et al. | 128/401 |
| 4,497,313 | 2/1985 | Kurosawa | 128/24.1 |
| 4,680,822 | 7/1987 | Fujino et al. | 128/399 |

FOREIGN PATENT DOCUMENTS

| 3012150 | 10/1980 | Fed. Rep. of Germany . |
| 3323365 | 3/1984 | Fed. Rep. of Germany . |
| 3532604 | 3/1986 | Fed. Rep. of Germany . |
| 55-130640 | 10/1980 | Japan . |
| 61-136714 | 8/1986 | Japan . |
| 61-170477 | 8/1986 | Japan . |
| 61-232868 | 10/1986 | Japan . |

Primary Examiner—Edward M. Coven
Assistant Examiner—Mark J. Graham
Attorney, Agent, or Firm—Frishauf, Holtz, Goodman & Woodward

[57] ABSTRACT

Thermotherapy apparatus used for performing a thermotherapy for a diseased part of a tumor such as a cancer of a living body. A heating portion is arranged in a distal end portion at the body cavity side of a probe which can be inserted in the body cavity through an endoscope or the like or a distal end portion at the body cavity side of an insertion portion of the endoscope. The heating portion has a far-infrared radiation ceramic member, and a heater for heating the far-infrared radiation ceramic member.

20 Claims, 7 Drawing Sheets

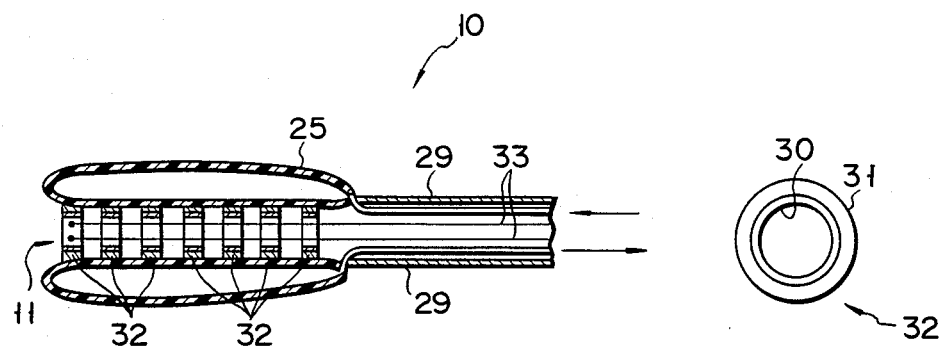
FIG. 15
FIG. 16
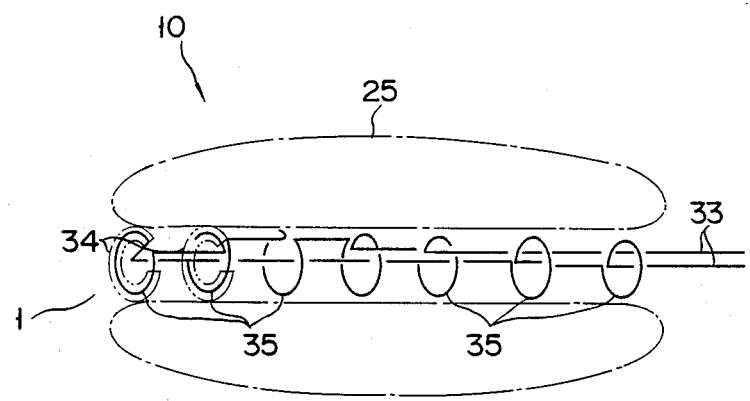
FIG. 17
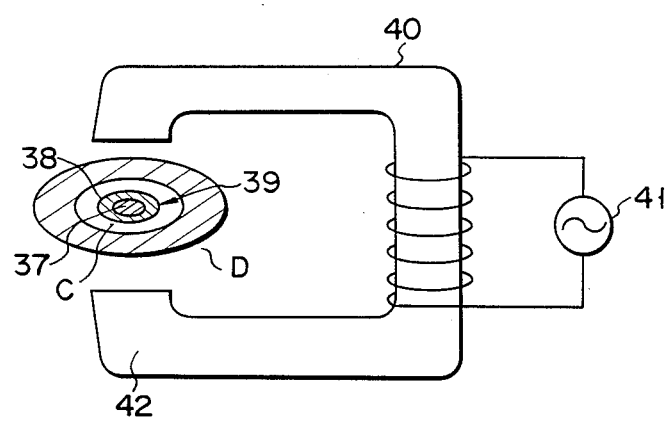
FIG. 18

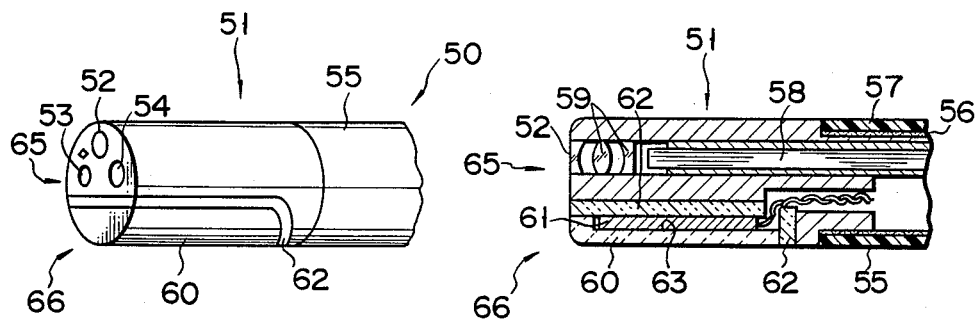
FIG. 19  FIG. 20
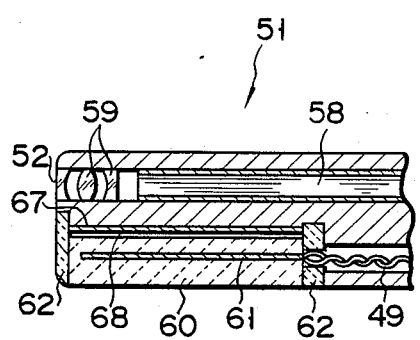 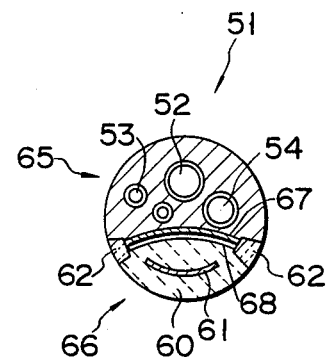
FIG. 21  FIG. 22
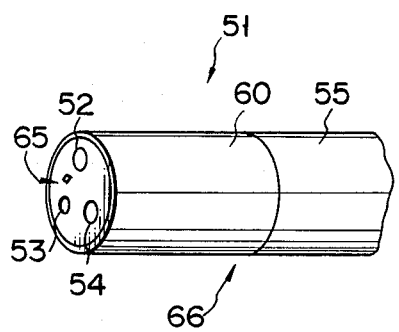 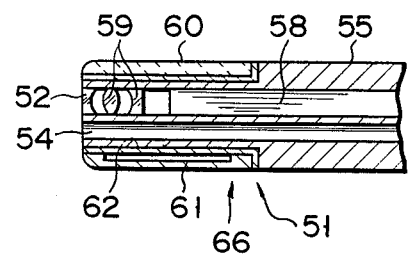
FIG. 23  FIG. 24

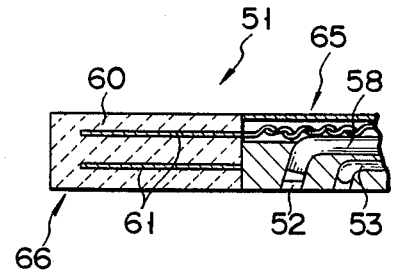
F I G. 26
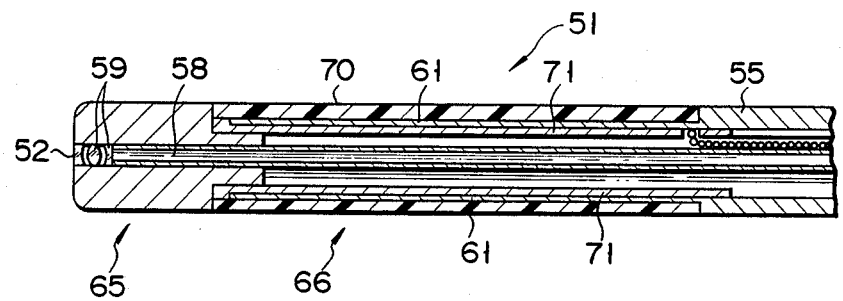
F I G. 27
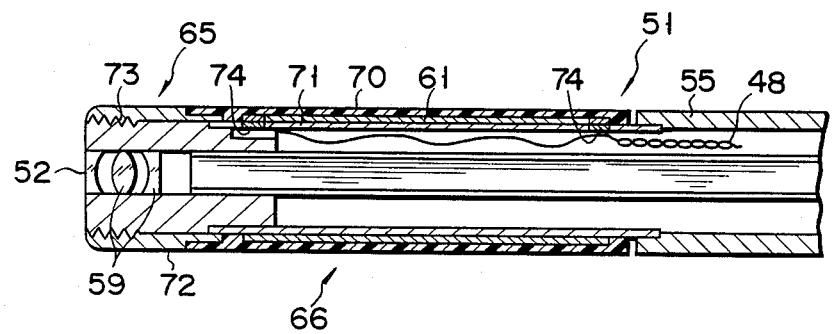
F I G. 28
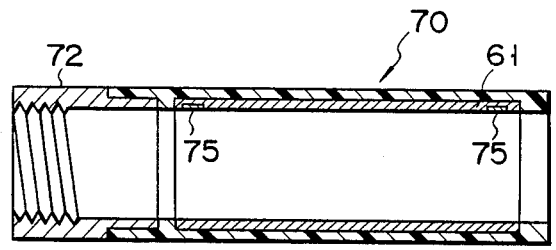
F I G. 29

THERMOTHERAPY APPARATUS

BACKGROUND OF THE INVENTION

The present invention relates to a thermotherapy apparatus for performing a thermotherapy of a tumor such as a cancer of a living body.

As a therapy for a cancer, a thermotherapy for heating a diseased portion and killing cancer tissue is known. The thermotherapy can be performed by using an endoscope having an insertion portion, and an operation portion for controlling the insertion portion. The insertion portion of the endoscope is inserted in a body cavity suffering from a cancer, and then the distal end of a probe is moved close to the diseased part through a treatment tool insertion channel extending inside the insertion portion. Microwaves are radiated from the probe to the diseased portion to heat it.

Japanese Patent Disclosure (Kokai) No. 55-130640 filed by the assignee of the present invention describes an endoscope wherein an infrared radiation apparatus is mounted in the distal end portion of an insertion portion, for radiating infrared rays to the diseased portion.

However, in the former case, since a heating range (depth) by the microwave is narrow, it is difficult to heat the entire diseased part to a proper temperature. In the latter case, since infrared rays of various wavelengths are radiated at the same time, they cannot be efficiently generated. Therefore, it is difficult in both cases to perform effective thermotherapy for a diseased part.

SUMMARY OF THE INVENTION

It is an object of the present invention to provide a thermotherapy apparatus which is free from the problems inherent in the conventional apparatuses, and can effectively perform a thermotherapy for a diseased part in a body cavity.

According to the present invention, a thermotherapy apparatus comprises a prove which can be inserted in a body cavity through an endoscope or the like, said probe having a distal end portion which can project into the body cavity through said endoscope or the like, and a heating potion provided in said distal end portion, and having a far-infrared radiation ceramic member and a heater for heating said far-infrared radiation ceramic member.

A heating portion at the distal end portion of the probe can be guided near a diseased part in a body cavity through a conventional endoscope, and thereafter, the far-infrared radiation ceramic member of the heating portion is heated by the heater. Far-infrared rays with high absorption property can be generated from the heating portion of the probe, and the diseased part can be effectively subjected to a thermotherapy.

The heater can comprise a laser or PTC element as a heat source.

The heater can determine whether the rays are radiated in the axial direction of the probe or in the lateral direction perpendicular thereto. The thermotherapy apparatus can, therefore, heat the diseased part properly in accordance with the position of the diseased part.

When a balloon is mounted on the outer surface of the heating portion of the probe, the heating portion can be prevented from directly contacting an inner wall of the diseased part.

When rings are formed by the far-infrared radiation ceramic member and the heater, and are arranged at equal intervals along the axis of the probe, a flexible heating portion can be formed, and the endoscope can be easily inserted.

According to another aspect of the present invention, a thermotherapy apparatus comprises an endoscope having an elongated insertion portion inserted in a body cavity, said insertion portion having a flexible portion through which a light guide and an image guide for observing an interior of the body cavity extend, and a distal end portion coupled to the body cavity side of said flexible portion, said distal end portion having a heating portion for heating an observation portion for observing an interior of the body cavity, and heat-shielding means for preventing thermal transmission between said observation portion and said heating portion, and said heating portion having a far-infrared radiation ceramic member and a heater for heating the far-infrared radiation ceramic member.

In this thermotherapy apparatus, the observation portion of the insertion portion can be arranged close to a diseased part in a body cavity. The far-infrared radiation ceramic member of the heating portion is heated by the heater, thus applying an effective thermotherapy to the diseased part.

An electrical heater may be embedded in the far-infrared radiation ceramic member. In this case, the ceramic member can be effectively heated, and the diseased part can be effectively treated.

The insertion portion may comprise a flexible heating tube formed of a heat-resistant material such as a polytetrafluoroethylene. The heating tube has many small holes in at least a portion, and far-infrared radiation ceramic sintered bodies are filled in these small holes. Since the heating portion is flexible, the diseased portion at a bent portion can be efficiently subjected to a thermotherapy.

Other features and advantages of the present invention will be apparent from the following description taken in conjunction with the accompanying drawings.

BRIEF DESCRIPTION OF THE DRAWINGS

FIG. 15 is a sectional view wherein a far-infrared radiation ceramic member and a heating heater are formed into ring shape, and a large number of rings are arranged along the axial direction of a probe;

FIG. 16 is a view showing the ring when viewed from a direction perpendicular to the surface of the drawing of FIG. 15;

FIG. 17 is a view of a 14th embodiment wherein a heater is formed into a wire shape;

FIG. 18 is a schematic view of an apparatus for heating from a deep portion of a living body by far-infrared rays;

FIG. 19 is a view for explaining a principal part of a first embodiment of a thermotherapy apparatus according to another aspect of the present invention;

FIG. 20 is a sectional view showing an internal structure of the embodiment shown in FIG. 19;

FIG. 21 is a sectional view showing an internal structure of a second embodiment according to another aspect of the present invention;

FIG. 22 is a sectional view when viewed from a direction perpendicular to the surface of the drawing in the embodiment of FIG. 21;

FIG. 23 is a view, similar to FIG. 19, of the second embodiment according to another aspect of the present invention;

FIG. 24 is a view, similar to FIG. 20, of the embodiment shown in FIG. 23;

FIGS. 25, 26, 27, and 28 are views, similar to FIG. 20, of fourth, fifth, sixth, and seventh embodiments according to another aspect of the present invention; and FIG. 29 is a sectional view wherein an internal structure of the seventh embodiment is omitted.

DESCRIPTION OF THE PREFERRED EMBODIMENTS

Figure 1:
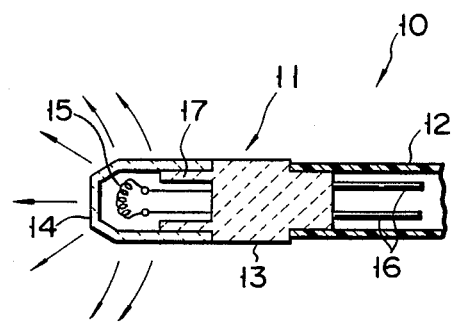
FIG. 1 is a sectional view for explaining a principal part of a thermotherapy apparatus according to a first embodiment of the present invention.
Figure 2:
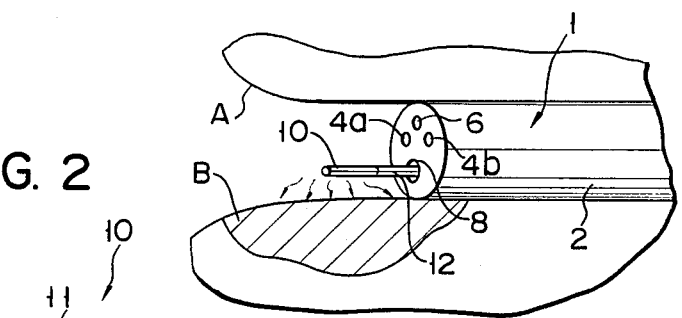
FIG. 2 is a view illustrating a state wherein a diseased part in a body cavity is subjected to a thermotherapy using the thermotherapy apparatus.

As shown in FIGS. 1 and 2, a thermotherapy apparatus according to the first embodiment comprises probe 10 which can be inserted in a body cavity through normal endoscope 1.

In this embodiment, endoscope 1 has elongated flexible insertion portion 2 inserted in body cavity A, and an operation portion (not shown) for operating the insertion portion. Light guide 4a, image guide 4b, air/water supply hole 6, and treatment tool through hole 8 extend inside insertion portion 2.

Probe 10 of the thermotherapy apparatus in this embodiment can be freely inserted in body cavity A through treatment tool through hole 8 of endoscope 1. The probe has elongated guide tube 12 of a flexible material, and heating portion 11 arranged at the distal end of the guide tube at the side of body cavity A, as shown in FIG. 1. Guide tube 12 guides heating portion 11 projecting into body cavity A via through hole 8 to a required position.

Heating portion 11 is constituted by mounting member 13 mounted on the distal end of guide tube 12, far-infrared radiation ceramic member 14 mounted on the distal end of the mounting member, and electric heater 15 arranged inside the ceramic member and located at a position at the distal end side of mounting portion 17 (to be described later). Mounting member 13 is formed of a heat-resistant material such as ceramic or plastic and formed into a cylindrical shape having small-diameter portions at both ends in the axial direction. The small-diameter portion at the side of guide tube 12 is fitted in tube 12, and mounting portion 17 at the side of body cavity A is formed into a hollow shape. The base portion of ceramic member 14, which is formed into a cap-like shape, is mounted in the hollow small-diameter portion. The axial length of mounting portion 17 is smaller than that of the cylindrical portion of ceramic member 14 engaged with mounting portion 17. Therefore, the closed end portion and the entire peripheral portion adjacent to the closed end portion of ceramic member 14 are heated by heater 15.

Electric heater 15 arranged in cap-like ceramic member 14 is coupled to a power source (not shown) through lead wire 16 extending inside guide tube 12 and fixed in mounting member 13, and heats ceramic member 14. Lead wire 16 can hold heater 15 at a predetermined position inside ceramic member 14.

Ceramic member 14 is formed of a ceramic sintered body prepared such that a flux is mixed with a ceramic material, e.g., $Al_2O_3$, $ZrO_2$, $TiO_2$, or the like, having a high far-infrared radiation ratio, and the mixture is sintered. A method of manufacturing a ceramic sintered body and a molding method to a predetermined shape are known, and a detailed description thereof will be omitted.

When probe 10 is assembled, an appropriate method can be employed as long as earth leakage from the interior of probe 10 can be prevented.

A thermotherapy using the thermotherapy apparatus described above is performed as follows.

As shown in FIG. 2, insertion portion 2 of endoscope 1 is inserted in body cavity A, and its distal end is arranged near diseased part B to be treated. Thereafter, probe 10 is inserted via through hole 8 from the operation portion (not shown), and heating portion 11 at the distal end of probe 10 is moved near diseased part B while observing the inner wall of body cavity A through an observation window. Thereafter, a current is supplied to heater 15 through lead wire 16 to energize heater 15, thus heating ceramic member 14. Thus, far-infrared rays are efficiently radiated from ceramic member 14 in the directions of arrows in FIG. 1, and a wide area of diseased part B is heated. In this case, since the therapy can be carried out while observing diseased part B using endoscope 1, excess heating of a normal tissue can be minimized, and effective therapy can be performed.

In this embodiment, probe 10 is inserted in body cavity A through conventional endoscope 1, and has been described in association with endoscope 1. However, the present invention is not limited to use with the conventional endoscope. For example, probe 10 constituting the thermotherapy apparatus of the present invention may be arranged to be inserted in a body cavity through a medical tool such as a gastroscope, a rectoscope, a laparoscope, and the like, whose distal ends can be inserted in body cavity A. In addition, probe 10 may be used together with these tools.

FIGS. 3 to 17 show second to 14th embodiments of probe 10. The same reference numerals in these embodiments denote the same parts as in FIGS. 1 and 2.

Figure 3:
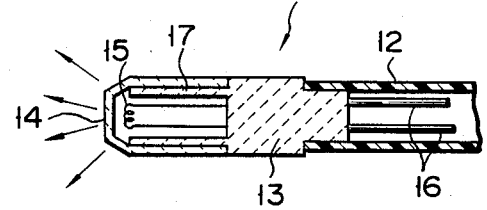
FIG. 3 is a sectional view of a second embodiment wherein far-infrared rays are mainly radiated in the axial direction of a probe.

In probe 10 of the second embodiment shown in FIG. 3, far-infrared rays are radiated from heating portion 11 mainly in the axial direction of probe 10.

Heating portion 11 in this embodiment is formed such that mounting portion 17 o mounting member 13 extends in the axial direction to surround heater 15. In probe 10 of this embodiment, the peripheral wall of a far-infrared radiation ceramic member is not heated, but only its distal end portion is heated. Thus, the far-infrared rays are radiated from the distal end portion of the probe mainly in the axial direction.

Figure 4:
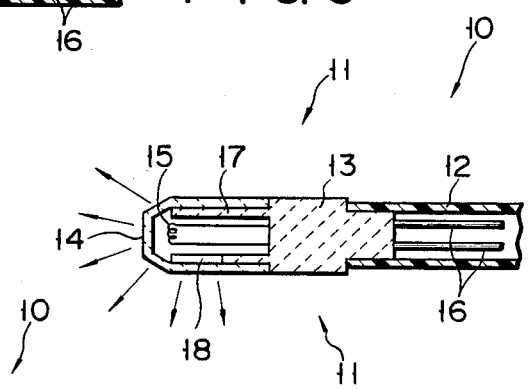
FIG. 4 is a sectional view of a third embodiment wherein far-infrared rays are radiated in both the axial direction and a direction perpendicular to the axial direction.

In probe 10 of the third embodiment shown in FIG. 4, notch 18 is formed on mounting portion 17 of mounting member 13, and the side wall of far-infrared radiation ceramic member 14 can be heated through the notch. According to heating portion 11 of this embodiment, far-infrared rays are radiated from a portion corresponding to notch 18 in the lateral direction as well as from the distal end portion in the axial direction.

Figure 5:
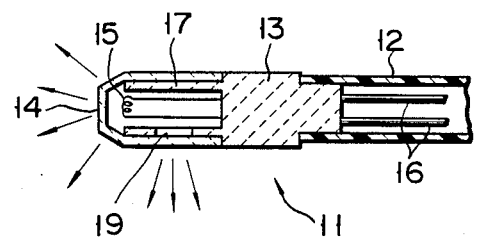
FIG. 5 is a sectional view of a fourth embodiment similar to the third embodiment.

In probe 10 of the fourth embodiment shown in FIG. 5, opening 19 is formed on the side wall of mounting portion 17 of mounting member 13. In heating portion 11 of this embodiment, far-infrared rays are radiated from the distal end portion and a portion corresponding to opening 19 as in the embodiment shown in FIG. 4.

Figure 6:
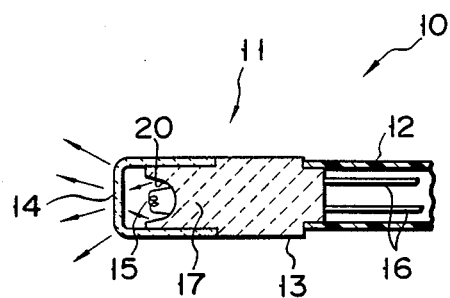
FIGS. 6 and 7 are respectively sectional views of fifth and sixth embodiments wherein heating efficiency of a far-infrared radiation ceramic member is improved.

In probe 10 of the fifth embodiment shown in FIG. 6, mounting portion 17 of mounting member 13 is formed to be solid, and recessed reflection surface 20 is formed at the distal end on the side of a body cavity. In heating portion 11 of this embodiment, heat generated by heater 15 is concentrated at the distal end portion of far-infrared radiation ceramic member 14 by reflection surface 20, and the ceramic member can be efficiently heated. Far-infrared rays are mainly radiated in the axial direction of probe 10.

Figure 7:
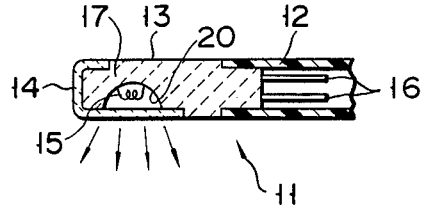

The arrangement of the sixth embodiment shown in FIG. 7 is substantially the same as that of the fifth embodiment, except that reflection surface 20 is formed on the side portion of mounting portion 17 of mounting member 13. In this embodiment, far-infrared rays are radiated mainly in the lateral direction perpendicular to the axial direction of probe 10.

Figure 8:
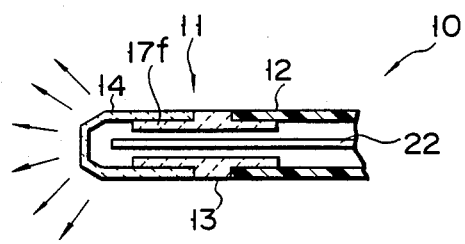
FIG. 8 is a sectional view of a seventh embodiment wherein a laser is used as a heat source.

In probe 10 of the seventh embodiment shown in FIG. 8, a laser is used as a heating source for far-infrared radiation ceramic member 14. Laser optical guide probe 22 extends from a laser beam source (not shown) in guide tube 12 and mounting member 13, and heats far-infrared radiation ceramic member 14. As is understood by those who are skilled in the art, a Zener diode (not shown) may be used as a heating member, as a matter of course.

Figure 9:
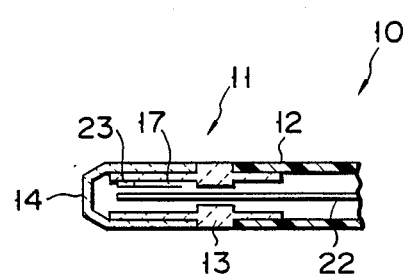
FIG. 9 is a sectional view showing a principal part of an eighth embodiment.

Probe 10 of the eighth embodiment shown in FIG. 9 adopts a laser beam supplied through laser optical guide probe 22 in the same manner as in probe 10 of the seventh embodiment. In this embodiment, temperature sensor 23 is mounted on mounting portion 17 of mounting member 13. Temperature sensor 23 detects a heating temperature of far-infrared radiation ceramic member 14, and sends a temperature signal to a control apparatus (not shown). The control apparatus keeps a heating temperature of the ceramic member at a desirable value. Thus, a radiation dose of the far-infrared rays can be maintained at a desirable value.

Figure 10:
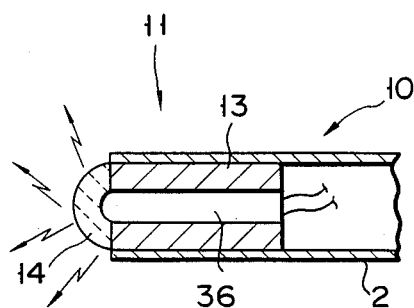
FIG. 10 is a sectional view of a ninth embodiment wherein a heater is constituted by a PTC element.

In probe 10 of the ninth embodiment shown in FIG. 10, PTC (Positive Temperature Coefficient) element 36 which has a self temperature control function as a heating member and a positive temperature characteristic is used in place of an electric heater.

Figure 11:
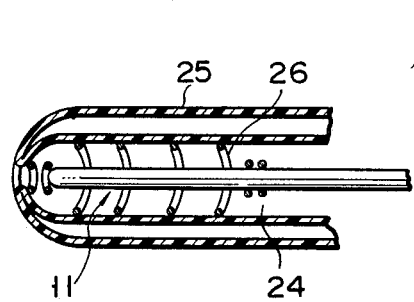
FIG. 11 is a view of a tenth embodiment wherein a balloon is mounted at the distal end of a probe.

In probe 10 of the 10th embodiment shown in FIG. 11, balloon 25 is detachably mounted on the outer surface of heating portion 11 through air layer 24. A fluid is supplied or removed to or from balloon 25 to hold probe 10 with respect to the inner wall of a body cavity.

Balloon 25 is mounted on the outer surface of heating portion 11 by coil spring 26 having a spindle shape, i.e., a cigar shape, the central portion of which has a larger diameter than two end portions in the axial direction. Coil spring 26 is held on probe 10 at the two-end small diameter portions so as to prevent balloon 25 mounted outside the coil spring from being in direct contact with probe 10. With this arrangement, the far-infrared radiation ceramic member can be efficiently heated, and efficiently generates far-infrared rays.

Note that the heater can adopt an appropriate energy source, such as an electric heater, a Zener diode, or a laser beam.

Figure 12:
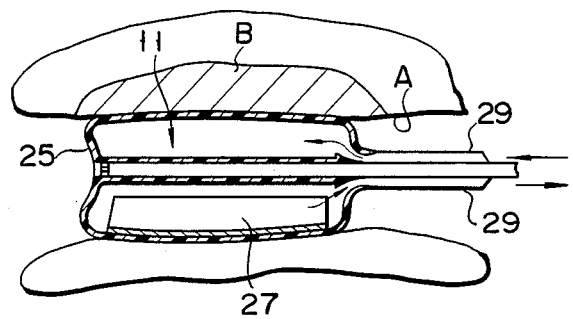
FIG. 12 is a sectional view of an 11th embodiment wherein a far-infrared reflection plate is arranged inside a balloon.
Figure 13:
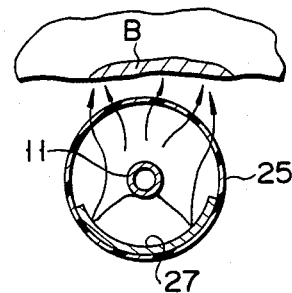
FIG. 13 is a sectional view when the surface of FIG. 12 is viewed from a direction perpendicular thereto.

In probe 10 of the 11 th embodiment shown in FIGS. 12 and 13, balloon 25 is mounted on the outer portion of heating portion 11 in the same manner as in the 10th embodiment. Tube 29 for supplying or removing a fluid communicates with balloon 25. Metal film 27 for reflecting far-infrared rays radiated from the peripheral portion of heating portion 11 toward one side of probe 10 is provided on the inner peripheral surface of balloon 25.

Probe 10 of this embodiment is effective when tumor B occurring on only one side of body cavity A is treated without heating normal tissues.

Figure 14:
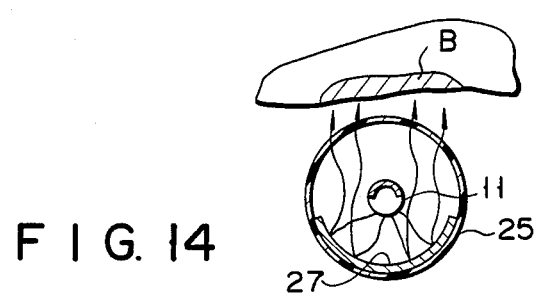
FIG. 14 is a view, similar to FIG. 13, showing a 12th embodiment wherein far-infrared rays are radiated from a probe only on a reflection plate.

The arrangement of probe 10 of the 12th embodiment shown in FIG. 14 is substantially the same as that of the probe of the 11th embodiment, except that far-infrared rays are radiated from heating portion 11 in only a direction toward metal film 27.

In probe 10 of the 13th embodiment shown in FIGS. 15 and 16, heating portion 11 has a large number of rings 32 constituted by a large number of annular heaters 30 arranged at equal intervals along the axial direction, and a large number of annular far-infrared radiation ceramic members 31 formed on the outer peripheral portions of heaters 30. A current is supplied to heaters 30 of rings 32 through wires 33. Heaters 30 convert electrical energy into thermal energy, and heat corresponding ceramic members 31 on their outer peripheral portions.

According to this embodiment, since a large number of rings 32 are formed by ceramic members 31 and heaters 30, heating portion 11 can be a flexible member. Thus, probe 10 can be easily inserted in the treatment tool through hole (FIG. 2) of endoscope 1, thus facilitating therapy.

Probe 10 according to the 14th embodiment shown in FIG. 17 has flexible heating portion 11 as in the probe of the 13th embodiment. In probe 10 of the 14th embodiment, a large number of ring-shaped heaters 35 formed by wires 33 are arranged along the axial direction. Far-infrared radiation ceramic members 34 are arranged on the surface portions of ring-shaped heaters 35. The extending positions of wires 33 of heaters 35 are slightly deviated in the peripheral direction of heaters 35, so that the ring-shaped heaters are not inclined on one side.

FIG. 18 shows an apparatus wherein far-infrared generating apparatus 39 comprising induction heating member 37 (ferromagnetic member such as ferrite) and far-infrared radiation ceramic member 37 arranged on the peripheral portion of the heating member is indwelt in body cavity C, and far-infrared rays can be generated from apparatus 39 by an AC magnetic field applied from the outside of human body D. When human body D and far-infrared generating apparatus 39 therein are placed in an AC magnetic field generated by core 40 and high-frequency power source 41, induction heating member 37 is heated, and ceramic member 38 radiates far-infrared rays from a deep portion of the human body.

Another thermotherapy apparatus will be described below.

FIGS. 19 and 20 show a first embodiment of a second thermotherapy apparatus. The thermotherapy apparatus of this embodiment comprises an endoscope having elongated flexible insertion portion 50 inserted in a body cavity, and an operation portion of a conventional structure (not shown) for operating the insertion portion. Distal end portion 51 of insertion portion 50, which is inserted in a body cavity, has observation portion 65 shown in the upper portion of FIGS. 19 and 20 and heating portion 66 shown in the lower portion thereof. Observation portion 65 and heating portion 66 are formed to have a semi-cylindrical shape, and are combined to form cylindrical distal end portion 51.

Observation portion 65 of distal end portion 51 has observation window 52, illumination window 53, and treatment tool through hole 54. Windows 52 and 53 are respectively optically connected, through lens 59, to image guide 58 and a light guide (not shown) extending in flexible portion 55 formed by covering the outer surface of braid 56 by sheath 57. Through hole 54 also communicates with a through channel (not shown) extending in flexible portion 55.

Heating portion 66 of distal end portion 51 has far-infrared radiation ceramic member 60 and electric heater 61 for heating the ceramic member. Ceramic member 60 is formed of a ceramic sintered body prepared by sintering a ceramic material having a high far-infrared radiation ratio, as described above.

Recess 63 is formed on the flat surface of ceramic member 60 of the first embodiment on the side of observation portion 65. Electric heater 61 is fitted in recess 63. Heat-shielding means, i.e., heat-shielding member 62, for preventing heat transmission between ceramic member 60 and observation portion 65, is provided therebetween. Thus, observation portion 65, in particular, image guide 58 therein, can be protected from heat.

Thermotherapy using the thermotherapy apparatus is performed as follows.

Insertion portion 50 is inserted in a body cavity, and far-infrared radiation ceramic member 60 is arranged at an appropriate position with respect to a diseased part through the operation portion while observing a portion to be treated. A current is supplied to electric heater 61 to energize it. Ceramic member 60 is heated, and radiates far-infrared rays having a high absorption characteristic with respect to a human body. A part suffering from a cancer in a body cavity is heated while damage to normal tissues due to overheating can be minimized. Therefore, a diseased part can always be an observation object, and thermotherapy can be effectively performed.

In distal end portion 51 according to a second embodiment shown in FIGS. 21 and 22, observation section 65 is formed to have a crescent section, and heating portion 66 has a section combined with the chord of the crescent section. Reflection plate 67 for reflecting far-infrared rays and gap 68 are provided between far-infrared radiation ceramic member 60 and observation portion 65. Gap 68 is maintained at a predetermined distance by heat-shielding members 62 provided to the two ends in the axial direction and the two edges of ceramic member 60. In this case, if a concave surface at the side of observation portion 65 is polished to form a reflection surface, reflection plate 67 may be omitted.

FIGS. 23 and 24 show distal end portion 51 according to a third embodiment. In distal end portion 51, heating portion 66 is provided around cylindrical observation portion 65. In this embodiment, far-infrared rays can be radiated along the entire peripheral surface of distal end portion 51.

Figure 25:
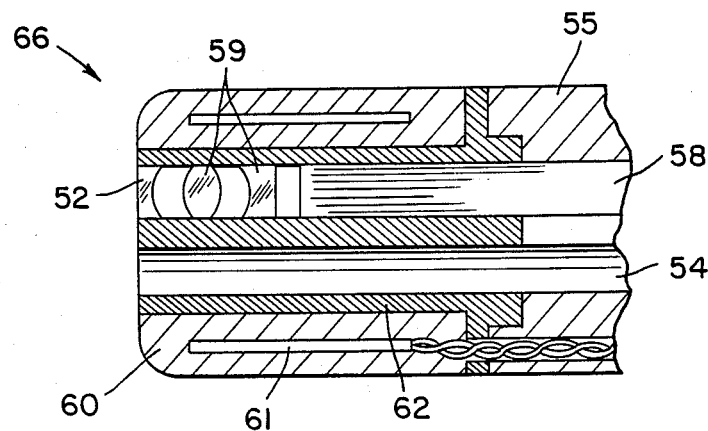

In distal end portion 51 according to a fourth embodiment shown in FIG. 25, an outer sheath is formed by far-infrared radiation ceramic member 60. Electric heater 61 is embedded in ceramic member 60 over the entire periphery of distal end portion 51. Far-infrared rays can be radiated from the entire peripheral portion of distal end portion 51 in the same manner as in the third embodiment.

Distal end portion 51 according to a fifth embodiment shown in FIG. 26 comprises observation portion 65 having observation window 52 directed in a direction perpendicular to the axis of the distal end portion and illumination window 53, and heating portion 66 mounted at the body cavity side of the observation portion. Far-infrared radiation ceramic member 60 of heating portion 66 is formed to have a cylindrical shape, and electric heater 61 is embedded therein. Heating portion 66 can be arranged at the side of the operation portion (not shown) opposite to the illustrated position.

Distal end portion 51 according to a sixth embodiment shown in FIG. 27 comprises flexible heating portion 66 coupled to the distal end of flexible portion 55 at the side of a body cavity, and observation portion 65 formed on heating portion 66 at the side of the body cavity.

Heating portion 66 comprises flexible heating tube 70 formed of a heat-resistant resin such as polytetrafluoroethylene, and image guide 58 is inserted therethrough. At least a portion of heating tube 70 is formed to be a sponge-like or foamed member having a large number of pores, or a large number of micropores are formed at least in a portion by machining. A far-infrared radiation ceramic sintered body is filled in the micropores. If the ceramic sintered body is locally filled, when a diseased part formed on one side of a body cavity is to be heated, normal tissues can be prevented from damage.

Electrical heater 61 formed to be a planar heating member is mounted inside flexible tube 70. Protective layer 71 for protecting image guide 58 therein from heat is provided inside the tube of heating portion 66.

In distal end portion 51 according to a seventh embodiment shown in FIGS. 28 and 29, heating tube 70 as in the sixth embodiment together with electric heater 61 is detachably mounted on flexible portion 55.

More specifically, one end of protective layer 71 is fixed to flexible portion 55, and the other end thereof is fixed to observation portion 65. In addition, electrical contact 74 of electrical lead wire 48 extending from a power source (not shown) is provided on the outer peripheral surface of layer 71. A male threaded portion is formed on the outer peripheral portions of observation 65 near observation window 52.

As shown in FIG. 29, heating tube 70 including electric heater 61 is formed on the outer peripheral surfaces of observation portion 65 and protective layer 71 to be fitted or removed therearound or therefrom. Cylindrical insulating member 72 is fixed to the end portion of heating tube 70 on the side of the body cavity. A female threaded portion is formed on the insulating member on the side of the body cavity to be threadably engaged with male threaded portion 73 of observation portion 65. Reference numeral 75 denotes an electrical contact which contacts electrical contact 74 to supply electrical power to electric heater 61.

Therefore, heating tube 70 is fitted around protective layer 71 and observation portion 65, and the threaded portions of observation portion 65 and insulating member 72 are threadably engaged with each other, thus allowing easy mounting. Upon removal, the operation opposite to the above is performed.

In this embodiment, electric heater 61 is mounted on heating tube 70, but can be fixed to flexible portion 55.

As is apparent from the above description, according to the present invention, a diseased part in a body cavity can be efficiently subjected to thermotherapy.

The present invention is not limited to the above embodiments, and various changes and modifications may be made within the spirit and scope of the invention.

What is claimed is:

1. A thermotherapy apparatus which is inserted in a body cavity through a medical tool in order to perform thermotherapy of a diseased part of a tumor in a living body, comprising;
   a probe sized for insertion in a body cavity through an endoscope, said probe having a distal end portion adapted to project into the body cavity through an endoscope;
   a heating portion provided in said distal end portion, and having a far-infrared radiation ceramic member and a heater for heating said far-infrared radiation ceramic member;
   wherein said probe has an elongated guide tube adapted to be inserted in an endoscope, and a mounting member, one end of which is fixed to a body cavity side of said guide tube, said far-infrared radiation ceramic member of said heating portion being mounted on the other end of said mounting member;
   wherein said far-infrared radiation ceramic member is formed to have a cap-like shape having a closed end portion at the side of a body cavity, said heater being arranged therein.

2. An apparatus according to claim 1, wherein said heater comprises an electric heater, and a conductive wire for supplying electrical power to said heater is inserted through said guide tube.

3. An apparatus according to claim 1, wherein said heater adopts a laser beam as a heat source, and a laser optical guide probe is arranged in said guide tube.

4. An apparatus according to claim 1, wherein said heater comprises a PTC element having a self temperature control function and a positive temperature characteristic.

5. An apparatus according to claim 2, 3 or 4, wherein said heater is directed with respect to said far-infrared radiation ceramic member so as to radiate far-infrared rays mainly in an axial direction of said probe.

6. An apparatus according to claim 2, 3 or 4, wherein said heater is directed with respect to said far-infrared radiation ceramic member so as to radiate far-infrared rays mainly in a direction perpendicular to an axial direction of said probe.

7. An apparatus according to claim 2, 3 or 4, which comprises a temperature sensor for controlling a heating temperature of said far-infrared radiation ceramic member, said temperature sensor being arranged inside said far-infrared radiation ceramic member.

8. An apparatus according to claim 1, which comprises a balloon detachably arranged to cover an end portion of said probe on the side of the body cavity, and a spindlelike-shaped coil spring for holding said balloon so as not to be in contact with said probe such that an air layer is formed between said balloon and said heating portion.

9. An apparatus according to claim 1, which comprises a balloon detachably arranged to cover an end portion of said probe on the side of the body cavity, and a reflection plate, arranged on said balloon on the side of said probe, for reflecting far-infrared rays toward one side of said probe.

10. An apparatus according to claim 1, wherein said heating portion comprises a plurality of rings constituted by annular far-infrared radiation ceramic members and annular heaters arranged therein, said rings being continuously arranged at equal intervals along an axial direction of said probe.

11. An apparatus according to claim 3, wherein said heater is directed with respect to said far-infrared radiation ceramic member so as to radiate far-infrared rays mainly in an axial direction of said probe.

12. An apparatus according to claim 4, wherein said heater is directed with respect to said far-infrared radiation ceramic member so as to radiate far-infrared rays mainly in an axial direction of said probe.

13. An apparatus according to claim 3, which comprises a temperature sensor for controlling a heating temperature of said far-infrared radiation ceramic member, said temperature sensor being arranged inside said far-infrared radiation ceramic member.

14. An apparatus according to claim 4, which comprises a temperature sensor for controlling a heating temperature of said far-infrared radiation ceramic member, said temperature sensor being arranged inside said far-infrared radiation ceramic member.

15. An apparatus according to claim 1, further comprising means for limiting emission of the far-infrared radiation to a predetermined angular range from said ceramic member.

16. A thermotherapy apparatus used for performing thermotherapy of a diseased part of a tumor in a living body, comprising:
   an endoscope having an elongated insertion portion inserted in a body cavity,
   said insertion portion having a flexible portion through which a light guide and an image guide for observing an interior of the body cavity extend, and a distal end portion coupled to the body cavity side of said flexible portion,
   said distal end portion having a heating portion for heating the diseased part, an observation portion for observing the interior of the body cavity, and heat-shielding means for preventing thermal transmission between said observation portion and said heating portion,
   said heating portion having a far-infrared radiation ceramic member and a heater for heating the far-infrared ceramic member;
   wherein said observation portion is formed to be able to observe a body cavity wall located in the axial direction of said insertion portion, and wherein said far-infrared radiation ceramic member of said heating portion is arranged on the entire peripheral portion of said observation portion, and said electric heater is embedded in said far-infrared radiation ceramic member.

17. A thermotherapy apparatus used for performing thermotherapy of a diseased part of a tumor in a living body, comprising:

an endoscope having an elongated insertion portion inserted in a body cavity;

said insertion portion having a flexible portion through which a light guide and an image guide for observing an interior of the body cavity extend, and a distal end portion coupled to the body cavity side of said flexible portion;

said distal end portion having a heating portion for heating the diseased part, an observation portion for observing the interior of the body cavity, and heat-shielding means for preventing thermal transmission between said observation portion and said heating portion; wherein said observation portion is formed to be able to observe a body cavity wall located in the axial direction of said insertion portion, and said far-infrared radiation ceramic member of said heating portion s arranged on at least a portion of the peripheral portion of said observation portion;

said heating portion having a far-infrared radiation ceramic member and a heater for heating the far-infrared ceramic member; and a reflection plate for reflecting far-infrared rays, said reflection plate being arranged between said far-infrared radiation ceramic member and said observation portion, and reflecting the far-infrared rays radiated from said far-infrared radiation ceramic member in an opposing direction of said observation portion.

18. A thermotherapy apparatus used for performing thermotherapy of a diseased part of a tumor in a living body, comprising:

an endoscope having an elongated insertion portion inserted in a body cavity;

said insertion portion having a flexible portion through which a light guide and an image guide for observing an interior of the body cavity extend, and a distal end portion coupled to the body cavity side of said flexible portion;

said distal end portion having a heating portion for heating the diseased part, an observation portion for observing the interior of the body cavity, and heat-shielding means for preventing thermal transmission between said observation portion and said heating portion; wherein said observation portion is formed to be able to observe a body cavity wall located in the axial direction of said insertion portion, and said far-infrared radiation ceramic member of said heating portion is arranged on at least a portion of the peripheral portion of said observation portion;

said heating portion having a far-infrared radiation ceramic member and a heater for heating the far-infrared ceramic member;

wherein said heating portion has a heating tube formed of a heat-resistant material, a large number of micropores being formed in at least a portion of said flexible tube, a far-infrared radiation ceramic material is filled in the micropores, and said heater is formed to be a planar heating member.

19. An apparatus according to claim 18, wherein said heating tube is detachably mounted on said flexible portion of said insertion portion, and said observation portion is detachably mounted on said tube.

20. An apparatus according to claim 19, wherein said heat-shielding means has a cylindrical protective layer, said protective layer being fixed to one of said flexible portion and said heating tube.

* * * * *